United States Patent [19]

Peoples et al.

[11] Patent Number: 5,480,794
[45] Date of Patent: Jan. 2, 1996

[54] OVERPRODUCTION AND PURIFICATION OF SOLUBLE PHA SYNTHASE

[75] Inventors: Oliver P. Peoples, Arlington; Tillman U. Gerngross, Cambridge; Anthony J. Sinskey, Boston, all of Mass.

[73] Assignee: Massachusetts Institute of Technology and Metabolix, Inc., Cambridge, Mass.

[21] Appl. No.: 290,131

[22] Filed: Aug. 12, 1994

Related U.S. Application Data

[63] Continuation-in-part of Ser. No. 71,574, Jun. 3, 1993, and a continuation-in-part of Ser. No. 234,721, Apr. 28, 1994, abandoned, which is a continuation of Ser. No. 73,603, Jun. 7, 1993, abandoned, which is a continuation of Ser. No. 944,881, Sep. 14, 1992, abandoned, which is a division of Ser. No. 700,109, May 8, 1991, Pat. No. 5,245,023, which is a continuation of Ser. No. 378,155, Jul. 10, 1989, abandoned, which is a continuation-in-part of Ser. No. 67,695, Jun. 29, 1987, abandoned.

[51] Int. Cl.$^6$ .............................. C12N 9/88; C12N 15/60
[52] U.S. Cl. .................... 435/232; 435/252.33; 536/23.2
[58] Field of Search ..................................... 435/232, 135, 435/252.3, 252.33; 536/23.2

[56] References Cited

U.S. PATENT DOCUMENTS

| | | | |
|---|---|---|---|
| 4,477,654 | 10/1984 | Holmes et al. | 528/361 |
| 5,245,023 | 9/1993 | Peoples et al. | 536/23.2 |
| 5,250,430 | 10/1993 | Peoples et al. | 435/232 |

OTHER PUBLICATIONS

Saggs, S. V., et al. (1981) Proc. Natl. Acad. Sci., U.S.A. 78(11), 6613–6617.
Spratt, S. K., et al. (1984) J. Bacteriol, 158(2), 535–547.
Young, R. A., et al. (1953) Proc. Natl. Acad. Sci., U.S.A. 80, 1194–1195.
Young, R. A., et al. (1953) Science 222, 775–787.
Peoples, O. P. et al. (1957) J. Biol. Chem. 262, 97–102.
Schubert, P., et al. (1988) J. Bacteriol. 170(12), 5837–5847.
Slater, S. C. et al. (1988) J. Bacteriol 170(10), 4431–4436.
Berg, D. E., et al. (1953) B. of Technology 1, 417–435.
Klechner, N., et al. (1977) J. Mol. Biol. 11, 125–159.
Ditta, G., et al. (1950) Pub. Natl. Acad. Sci. U.S.A. 77(12), 7347–7351.
Simon, R., et al. (1953) B. of Technology 1(9), 784–791.
Simon (1954) Mil. Gen, Gbnft 196, 413–420.
Senior and Dawes, *Biochemical Journal*, 134, 224–238 (1973).
Oeding and Schlegel, *Biochemical Journal*, 134, 239–248 (1973).
Berndt and Schlegel, *Arch. of Microbiol.*, 103, 21–30 (1975).
Nishimura, et al., *Arch. Microbiol.*, 116, 21–27, (1978).
Saito, et al., *Arch. Microbiol.*, 114, 211–217 (1977).
Fukui, et al., *Biochem. Biophys. Acta.*, 917, 365–371, (1987).
Fukui, et al., *Arch. Microbiol.*, 110, 149–156, (1976).
deSmet, et al., *Journal of Bacteriology*, 154(2), 870–878 (1983).
Schlegel, et al., *Arch. Microbiol.*, 71, 283–294 (1970).
K. Tomita, T. Saito, and T. Fukui "Bacterial Metabolism of Poly–beta–hydroxybutyrate" Greenbock–Lilly Symposium in Honor of Dr. H. A. Hardy, Jun. 9–11 (1982).
Peoples, O. P., et al. (1989) J. Biol. Chem. 264(26), 15198–15303.
Tomita, K., et al. (1992) Greenbock–Lilly symposium in Honor of Dr. H. A. Lardy.
Fukui, T. et al. (176) Arch Microbiol. 110, 149–156.
Gerngross, T. U., et al. (1994) Biochemistry 33(31), 9311–9320.
Griebel and Merrick, *J. Bacteriol.*, 108, 782–789 (1971).

*Primary Examiner*—Charles L. Patterson, Jr.
*Attorney, Agent, or Firm*—Arnall Golden & Gregory

[57] ABSTRACT

Purified, soluble recombinant bacterial long chain and short chain PHA synthases are described, with methods and materials for overexpression and purification.

23 Claims, 3 Drawing Sheets

FIG. 1a
```
           EcoR1       RBS
Primer 1: CC GAATTC AGGAGGTTTTTATT ATG-GCT-ACC-
           GGC-AAA-GGC-GCG-GCA-GCT-TCC-ACG-C
Primer 2: C-GTG-CAG-CGG-ACC-GGT-GGC-CTC-GGC-CTT-
          GCC-C
```
FIG. 1b
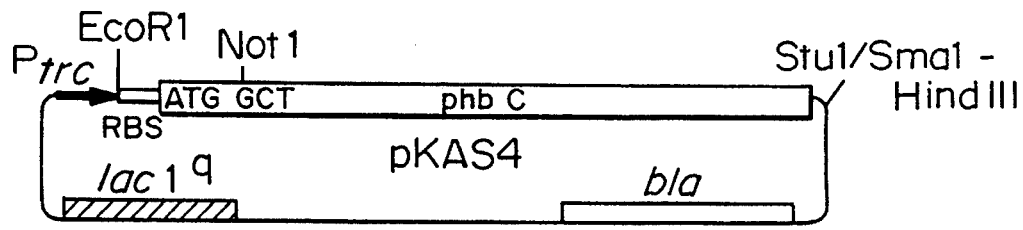
FIG. 2
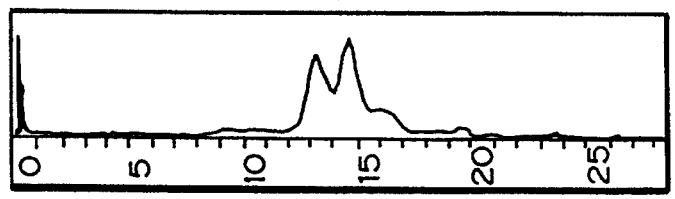
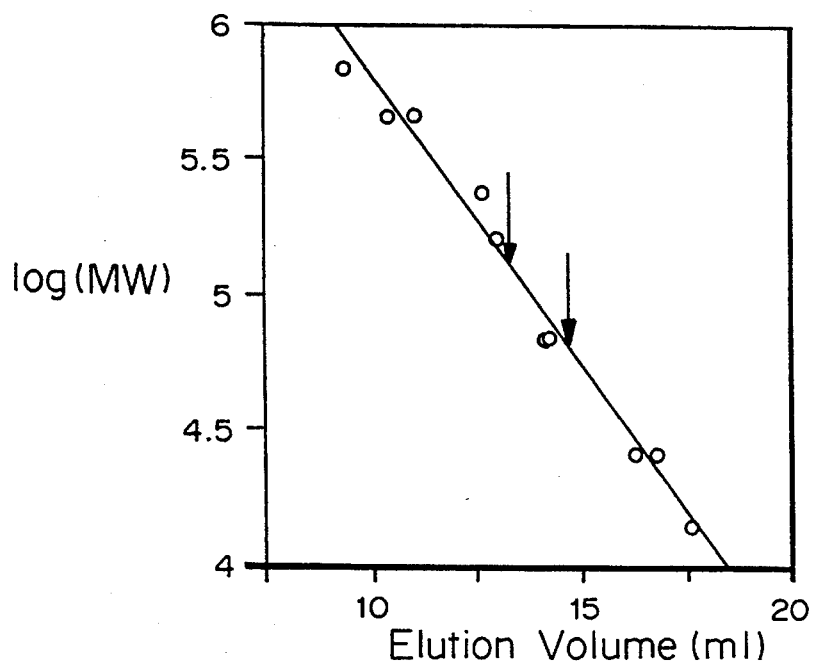

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (synthetic)

```
        ( i i i ) HYPOTHETICAL: NO ( i v ) ANTI-SENSE: NO ( x i ) SEQUENCE DESCRIPTION: SEQ ID NO:1:

CCGAATTCAG  GAGGTTTTTA  TTATGGCTAC  CGGCAAAGGC  GCGGCAGCTT  CCACGC                56

( 2 ) INFORMATION FOR SEQ ID NO:2:

( i ) SEQUENCE CHARACTERISTICS:
                ( A ) LENGTH: 32 base pairs
                ( B ) TYPE: nucleic acid
                ( C ) STRANDEDNESS: single
                ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:2:

CGTGCAGCGG  ACCGGTGGCC  TCGGCCTTGC  CC                                            32
```

OVERPRODUCTION AND PURIFICATION OF SOLUBLE PHA SYNTHASE

This is a continuation in part of U.S. Ser. No. 08/234,721 filed Apr. 28, 1994, abandoned, which is a continuation of U.S. Ser. No. 08/073,603 filed Jun. 7, 1993, abandoned, which is a continuation of U.S. Ser. No. 07/944,881 filed Sep. 14, 1992, abandoned, which is a divisional of U.S. Ser. No. 07/700,109 filed May 8, 1991, issued as U.S. Pat. No. 5,245,023, which is a continuation of U.S. Ser. No. 07/378,155 filed Jul. 10, 1989, abandoned, which is a continuation in part of U.S. Ser. No. 07/067,695 filed Jun. 29, 1987, by Oliver P. Peoples and Anthony J. Sinskey, abandoned. This is also a continuation in part of U.S. Ser. No. 08/071,574 filed Jun. 3, 1993, by Oliver P. Peoples and Anthony J. Sinskey. The teachings of these applications are specifically incorporated by reference herein.

The United States government has rights in this invention by virtue of National Science Foundation grant 9018546-BMB to J. Stubbe, S. Masamune, O. Peoples and A. J. Sinskey and ONR-N00014- 90-J-1529 to Oliver Peoples and A. J. Sinskey.

The use of enzymes as organic synthetic reagents is an area of increasing industrial interest (Jones, (1986) Tetrahedron. 42, 3351–3403; Wong, (1989) Science 244, 1145–1152). Cloning of the genes encoding individual enzymes enables production of reagent-type quantities of enzymes and modification of their properties, for example, temperature stability, pH stability, and substrate utilization, through the use of recombinant DNA technology.

The polyhydroxyalkanoate ("PHA") polymerases are unique biocatalysts capable of polymerizing up to thousands of monomeric units in a head to tail condensation to produce high molecular weight polymers. To date there have been no reports of the preparation of reagent quantities of the PHA polymerases, separated from the PHA granules to which they become attached in vivo, for use as biocatalysts to prepare novel polyester polymers, although the genes encoding these polymerases and their use are described in U.S. Pat. No. 5,245,023 to Peoples and Sinskey. By making these biocatalysts available, a range of polyesters can be prepared by combining organic synthesis of unique precursors with enzymatic polymerization.

The potential for utilizing biological systems as a source of biodegradable materials is becoming increasingly attractive in view of the environmental problems associated with disposal of traditional oil based polymers (Chu, (1985) CRC Crit. Rev. Biocompatibil., 1, 261–322; Agrawal, et al., (1992) Biomaterials, 13, 176–182; Tamada & Langer, (1993) Proc. Natl. Acad. Sci. U.S.A., 90, 552–556).

Poly-D-3-hydroxyalkanoates (PHAs) are polyoxoesters synthesized from optically active thiol esters that are produced in many types of bacteria (Anderson & Dawes, (1990) Microbiological Reviews, 54, 450–472); FEMS Microbiological Reviews, vol. 103 Schlegel, H. G. and Steinbuchel, A., editors (1992). Polyoxoesters have recently been found in mammalian systems as well (Reusch, et al., (1992) Biochim. Biophys. Acta, 1123, 33–40). Thus, these polymers are of interest from both biological and applied perspectives (Seebach, (1992) FEMS Microbiol. Rev., 103, 215); Muller & Seebach, (1993) Angew. Chem. Int. Ed. Engl., 32, 477–502).

Short chain PHAs, homo or co-polymers of four to five carbon units in which the monomeric building blocks are provided by (D)-3-hydroxybutyryl- and (D)- 3-hydroxyvaleryl-CoA, are particularly of interest. The biosynthetic pathways for these polyoxoesters have been most extensively investigated in Zoogloea ramigera (Tomita, et al., (1983) In: Biochemistry of Metabolic Processes., Leeon, D., Stratman, F. and Zahlten, R. (eds.), Elsevier Press: Holland, p. 353) and Alcaligenes eutrophus H16 (Slater, et al., (1988) J. Bacteriol., 170, 4431–4436; Schubert, et al., (1988) J. Bacteriol., 170, 5837–5847; Peoples & Sinskey, (1989) Molecular Microbiol., 3, 349–357; J. Biol. Chem., 264, 15293–15297; J. Biol. Chem., 264, 15298–15303, and U.S. Pat. No. 5,245,023). As discussed in more detail below, their biosynthesis involves three proteins: a thiolase, a reductase and a synthase for polymerase.

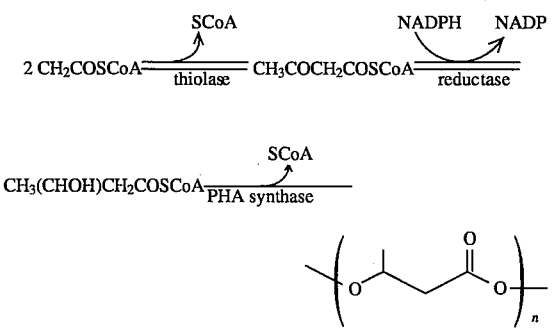

A large number of bacterial species have the ability to accumulate intracellular reserves of poly D-3-hydroxyalkanoates (PHAs). These polymers may constitute up to 80% of the dry cell weight of the bacterium and are found in storage granules (Anderson and Dawes, 1990). The polymers can be divided into two classes based on the number of carbon atoms in the monomeric units. Short chain PHAs (SCPHAs) are homo/copolymers of three to five carbon units and are typified by the PHAs produced by Alcaligenes eutrophus H16. Long chain PHAs (LCPHAs) contain subunits of six to 12 carbon atoms and are produced by Pseudomonads.

In the past few years, Peoples et al., (1987) J. Biol. Chem., 262, 97–102; (1989) J. Biol. Chem. 264, 15298–15303; J. Biol. Chem. 264, 15293–15297; Molecular Microbiol. 3, 349–357; Peoples and Sinskey, 1990; U.S. Pat. No. 5,245,023) have been successful in identifying both the genes and gene products responsible for the biosynthesis of SCPHAs from Zoogloea ramigera, A. eutrophus H16 and LCPHAs from Pseudomonas oleovorans.

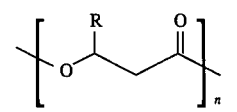

R = $C_3H_7$, $C_9H_{12}$
Pseudomonas oleovorans TF41L
LONG CHAIN PHAs

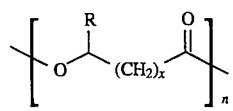

R = H, $CH_3$, $C_2H_5$
x = 1–3
A. eutrophus H16
SHORT CHAIN PHAs

The thiolases and reductases from *A. eutrophus* and *Z. ramigera* have been extensively studied from both biochemical and mechanistic perspectives (Masamune, et al., (1989) Pure Appl. Chem., 61, 303–312); Ploux, et al., (1988) Eur. J. Biochem., 174, 177–182; Peoples, et al., (1987) J. Biol. Chem., 262, 97–102). However, both the soluble and granule bound forms of the naturally occurring PHA synthase have resisted purification to a stable form which can be investigated (Haywood, et al., (1989) FEMS Microbiol. Lett. 57:1–6; Tomita, et al., (1983)).

The genes for all three enzymes from *A. eutrophus* have been cloned and expressed in *E. coli*. Sequence analysis reveals that the gene encoding the synthase is part of a biosynthetic operon containing the phbC-phbA-phbB genes coding for synthase-thiolase-reductase, respectively. The synthase is a protein of 63.9 kDa and its DNA sequence exhibits no homology with the DNA sequence of any previously reported proteins. The presence of all three genes in *E. coli* results in accumulation of large quantities of PHA (50% of the dry weight of the cell) (Slater, et al., (1988); Schubert, et al., (1988); Peoples & Sinskey, (1989)). Until recently, efforts to overexpress the synthase in the absence of the thiolase and reductase have proven unsuccessful.

It is therefore an object of the present invention to provide a method and means for overexpression of the soluble form of the synthase.

It is a further object of the present invention to provide a method for isolating, and the isolated, purified synthase in active form.

SUMMARY OF THE INVENTION

Two forms of soluble short chain PHA synthase (SCPHA) are disclosed in purified form, as well as a method for purification of recombinant SCPHA synthase overexpressed in another bacteria such as *E. coli*. As described in the example, the synthase is overexpressed by insertion of the gene encoding the synthase, under the control of a regulatable promoter, such as the IPTG inducible promoter, into an appropriate host, such as an ompT deficient *E. coli* strain, or *E. coli*, bacteria, plants, yeast, or fungi, which either do not produce protease cleaving the synthase or where the synthase is engineered to remove protease sensitive cleavage sites.

BRIEF DESCRIPTION OF THE DRAWINGS

FIG. 1a and 1b is a schematic of the construction of pKAS4 containing phbC from *Alcaligenes eutrophus*.

FIG. 2 is a graph of the molecular weight determination of native PHA synthase using Superdex™ G-200 size exclusion chromatography, plotting log (molecular weight) versus volume of elution from the Superdex™ column, in comparison with molecular weight standards (methods). Two different protein containing fractions containing synthase activity and cross-reacting with PHA synthase antibodies are shown by the arrows.

DETAILED DESCRIPTION OF THE INVENTION

Figure 3A:
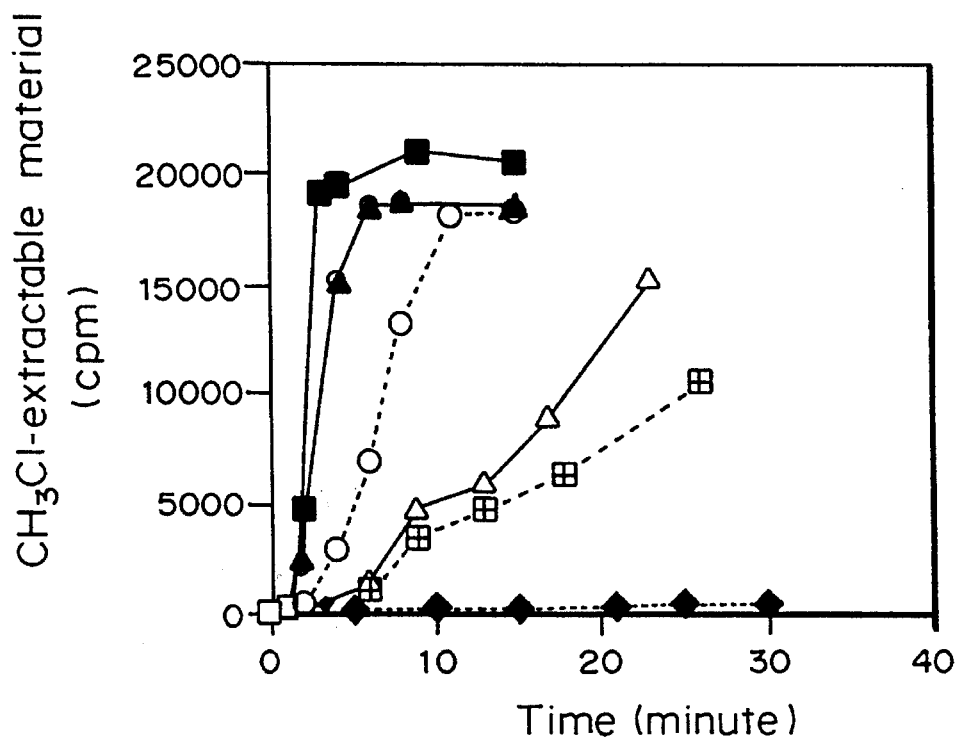
FIG. 3a is a graph of the rate of PHA formation as a function of time (minutes) and enzyme concentration: 0.07 µg (open diamonds); 0.17 µg (open squares); 0.35 µg (circles); 0.23 µg (open triangles); 0.07 µg (closed triangles); 1.4 µg (closed squares).

The functional expression in *E. coli* of the phbABC gene products encoding thiolase, reductase and synthase, respectively, required for the biosynthesis of PHA from *A. eutrophus*, has been described by Slater, et al., 1988; Schubert, et al., 1988; and Peoples & Sinskey, 1989. The transformation of *E. coli* with the phbC gene alone, does not result, however, in the production of polymer in a nitrogen starved medium. Using $^{35}$S-labeling studies in maxicells, Peoples and Sinskey (1989) reported that low levels of expression of a protein of approximately 64 kDa was observable by SDS-PAGE and that expression of this protein appeared to be correlated with production of very low levels of $CHCl_3$ extractable material upon incubation of [$^3$H]-HBCoA with these crude cell extracts. It would be desirable to overexpress the synthase in soluble form, in the absence of the thiolase and acetoacetyl CoA reductase, since the absence of these latter two gene products is desirable as they can use cellular acetylCoA to initiate the polymerization process leading to granule bound, insoluble synthase. Expression in the soluble form offers the advantage that the priming and initiation processes required for polymerization can be controlled.

The genes encoding both the SCPHA synthase and the LCPHA syntase are known. As described herein, however, are methods to increase production of the soluble synthase in the absence of the reductase and thiolase. These consist of:

1. Expression in an appropriate system
   expression in a host expression system not including proteases cleaving the soluble syntase, including bacteria other than *E. coli* which express the ompT gene such as Bacilllus, Pseudomonads, and Coryneforms (Methods in Enzymology, vol. 185), yeast such as Saccharomyces and Kluvyeromyces for which methods are known to those skilled in the art (Methods in Enzymology vol. 194); and fungi such as Aspergillus, Neurospora and Trichoderma for which methods are known to those skilled in the art, as described in Applied Molecular Genetics of Fungi, Peberdy, Caten, Ogden, and Bennett, eds. (Cambridge University Press, N.Y. 1991), many of which can be obtained from the American Type Culture Collection, Rockville, Md., which are routinely used by those skilled in the art; and plants such as oilseed crops including rapeseed, canola, sunflower, soybean, cottonseed, and safflower, for which methods are known to those skilled in the art (Gasser and Fraley, 1989 Science 244:1293–1299; or expression in a host system which expresses protease where the synthase gene is modified to not include proteolytic cleavage sites, as described in detail below in the examples below.

2. Expression under the control of a regulatable promoter
   many regulatable promoters and chemically inducible promoters such as the IPTG inducible promoters are known, including the lacZ, tac, the trp promoter, the temperature inducible phage promoter lambda $P_L$ and the phage T7 promoter/T7 RNA polymerase system, and osmotic sensitive promoters.

3. Other modifications to increase efficiency of expression alteration of the ribosome binding site to substitute a ribosome binding site specific to the host expression system.

Genetic Engineering of Organisms to overexpress soluble SCPHA Polymerase Biocatalyst The identification of the phbC gene encoding the *A. eutrophus* H16 SCPHA polymerase, described in U.S. Pat. No. 5,245,023, enables the overproduction of the functional gene product in *Escherichia coli*. As described in detail in the following examples, plasmid pKAS4 was constructed as illustrated below. The ribosome-binding (RBS) region of the phbC structural gene was modified using PCR to optimise this region for translation in *E. coli* and inserted into a modified version of the trc expression vector pTrc99A (Amann et. al., 1988). The original vector was modified by digesting with the restriction enzyme Nco 1 and treatment with S1-nuclease to generate blunt ends prior to religating. The net effect of these manipulations is to destroy the Nco 1 site and remove the ATG start codon contained within it. The phbC structural gene with the added efficient ribosome binding site ("RBS") was inserted into the Eco R1 site of this plasmid to obtain plasmid pKAS4.

*E. coli* JM105 cells carrying plasmid pKAS4 express significant levels of functional SCPHA polymerase following induction with isopropyl-β-D-thiogalactoside (IPTG). This activity decreases rapidly in lysed cells and immunoblot analysis of the overproduced SCPHA polymerase protein indicates that the full-length, 64 kd polypeptide is being specifically cleaved to yield a 50 kd protein. N-terminal amino acid sequence analysis of the truncated polypeptide identified the site of cleavage between the arginine residues, Arg 100 and Arg 101, of the polypeptide sequence. This sequence of residues is one of the sequences cleaved by the *E. coli* outer membrane protease VII encoded by the ompT gene (Sugimara and Nishihara, (1988) J. Bacteriol. 170, 5625–5632).

The plasmid pKAS4 was therefore transferred into the ompT deletion mutant strain UT5600 (Fiss et. al., (1979) Biochem. Biophys. Res. Commun. 91, 29–34). In this strain, rapid degradation of the SCPHA polymerase protein is eliminated, resulting in lysed cells with high levels of stable SCPHA polymerase activity suitable for use as a biosynthetic reagent for the synthesis of novel polyesters.

As described in Example 1, PHA synthase was expressed in *Escherichia coli* by re-engineering the 5'-end of the wild-type (wt) gene and subsequent transformation of this gene into protease deficient *E. coli* UT5600 (ompT⁻). Induction with IPTG results in soluble PHA synthase which is approximately 5% of the total protein.

Purification of Soluble PHA synthase

A cell lysate is prepared at 4° C. The supernatant or crude filtrate is isolated, filtered through a 0.45 µm membrane, made 0.05% (w/v) in Hecameg™ and loaded directly onto a hydroxylapatite column equilibrated in glycerol (one to fifteen percent/volume to volume, preferably 5%) KPi (10 to 50 mM, pH 6–8, preferably 7), and Hecameg™ (0.01 to 2% w/v, preferably 0.05%). The column is washed with Hecameg™-glycerol buffer and eluted with a linear gradient from 10 to 300 mM KPi in Hecameg™-glycerol buffer. The synthase elutes between 110 and 150 mM KPi. The fractions containing activity can be pooled and rapidly frozen (liquid nitrogen) without significant loss in activity. This material can be directly loaded onto a Q-Sepharose™ high performance FPLC column equilibrated with Hecameg™-glycerol buffer, pH 8.5 at 4° C. Subsequent to loading, the column is washed and a linear gradient from 0 to 1.5 M NaCl in Hecameg™-glycerol is then applied. Greater than 90% of PHA synthase elutes in fractions 2 and 3. Approximately 10% of the protein elutes in fractions 11 and 12 at 500 mM NaCl. The fractions are pooled and concentrated using a YM 30 membrane and an Amicon filtration apparatus. The protein is then rapidly frozen in liquid nitrogen and stored at −80° C. The protein is stable for at least a month under these conditions.

FPLC, providing rapidity of purification, and a variety of anion exchange materials including hydroxylapatite and Q-Sepharose™, can be used to purify the synthase to greater than 90% homogeneity with a 40% recovery of overall units. Based on Coomassie staining of the protein in the crude cell extracts subsequent to SDS-PAGE, it was anticipated that a purification of approximately 20 fold would be required to obtain homogeneous protein. The protein isolated from the Q Sepharose™ column has a specific activity of 5 µmol min⁻¹ mg⁻¹ and upon freezing and thawing its activity increases to 8 µmol min⁻¹ mg⁻¹, a 16-fold overall purification. The enzyme is stable when rapidly frozen in liquid nitrogen for a period of at least a month.

This procedure yields a soluble synthase purified to greater than 90% homogeneity with a specific activity of 5 µmol min⁻¹ mg⁻¹. The molecular weight of the PHA product is approximately $10^6$ Da based on PlGel chromatography and calibration using polystyrene molecular weight markers. The synthase, in the absence of substrate, appears to exist in both monomeric and dimeric forms. Incubation of the synthase with an excess of substrate converts it into a form that is now extractable into $CHCl_3$ and sediments on sucrose density ultracentrifugation with PHA. Studies in which the ratio of substrate, 3-D-hydroxybutyrylCoA, to synthase is varied suggest that during polymerization, the elongation process occurs at a rate much faster than the initiation process.

In contrast to expectations based on previous attempts to purify the soluble synthase (Haywood, et al., 1989; Tomita, et al., 1983), the enzyme is stable when rapidly frozen at liquid $N_2$ temperatures and stored at −80° C.

Initial efforts to characterize the synthase focused on determination of the size distribution of [³H]-PHA polymers using a variety of size exclusion chromatographic systems including Showdex™, PlGel™ and/or Sephacryl™ columns. These efforts resulted in minimal recovery of [³H]-polymer from these columns. Apparently the protein-polymer complex either precipitates on the top of the columns and/or tightly binds to a wide variety of different column backbone matrices. However, treatment of the PHA-synthase complex with pronase followed by analysis on a PlGel™ column resulted in recovery of 40% of the radioactivity in a polymer of molecular weight $^{-}10^6$ Da. This molecular weight has been assigned based on comparison with polystyrene polymer standards. Additional studies on the PHA·synthase complex using sucrose gradient ultracentrifugation revealed formation of very large molecular weight aggregates as well. Thus, the synthase in vitro is capable of producing polymers at least as large as those isolated from *A. eutrophus* and these polymers appear to behave as a granule bound synthase.

The kinetics of PHB formation obtained using the standard assay gave very different results from those previously reported in the literature by Tomita, et al., 1983; Haywood, et al., 1989. The formation of polymer is preceded by a long and variable lag time. Furthermore, the rate of polymer formation, measured subsequent to the lag, has a non-linear dependence on enzyme concentration up to 0.2 µM PHA synthase. This lag phase can be associated in some way with the priming and initiation process required for polymerization. Similar lag phases have been detected with glycogen synthase and rubber polymerase when the appropriate primers are lacking (Smythe and Cohen, (1991) Eur. J. Biochem., 200, 625–631; Light, et al., (1989) J. Biol. Chem., 264, 18589–18597; Light, et al. (1989) J. Biol. Chem., 264, 18598–18607). The priming process might well require conversion of a monomeric to a dimeric form of the synthase, consistent with two forms of the protein detected by size exclusion chromatography. In synthases isolated from their normal hosts, either PHB granules, in the case of the insoluble synthases, or small amounts of oligomers of PHB, in the case of the soluble synthases, could be present and serve as primers. Thus, the enzymes as isolated from their natural hosts may have been preprimed and thus, no lag phase is detectable (Tomita, et al., 1983). The observation that the lag phase is removed by preincubation of the recombinant synthase with cold 3-D-HBCoA for 10 minutes prior to addition of the [$^3$H]-HBCoA is consistent with this model.

A set of experiments in which the synthase is incubated with varying ratios of 3-D-HBCoA per synthase (up to 10,000 to 1), followed by analysis of the products by ultracentrifugation, indicates that most of the synthase is active and can produce polymer.

The present invention will be further understood by reference to the following non-limiting examples.

Example 1: Modification and overexpression of PHA synthase in protease-deficient E. coli.

Materials and Methods

Coenzyme A, glucose-6-P dehydrogenase (specific activity 50 to 150 µmol min$^{-1}$ mg$^{-1}$), pronase, and NADPH, were obtained from Sigma. NcoI, EcoRI, NotI, SmaI, molecular weight standards, and T4 DNA Ligase were obtained from Gibco BRL. [1-$^3$H]-Glucose (15.5 curie/mmol) and [$^{35}$S] ATPYS (1000 millicurie/mmol) were obtained from New England Nuclear. IPTG was obtained from Boehringer Mannheim. 6-O-(N-heptylcarbamoyl)-methyl-α-D-glucopyrano-side (Hecameg™) was obtained from Vegatec, Villejuif, France. Q-Sepharose™ was purchased from Pharmacia and Macro-prep™ hydroxylapatite 18/30 (binding capacity of 12 mg of lysozyme/g) was a gift of Dr. Larry Cummings, Bio-Rad Laboratories Inc. PlGel Mixed C (5µ) column was purchased from Polymer Laboratories (Amherst, Mass.). ClS-Sep-Pak cartridges were from Waters Inc. The Klenow fragment of DNA polymerase was obtained from Amersham. The oligonucleotides were synthesized by the MIT Biopolymers Laboratory and used without further purification. HydroxybutyrylCoA (HBCoA) was synthesized using A. eutrophus acetoacetylCoA reductase, (20 units mg$^{-1}$) as described by Ploux, et al., 1988).

E. coli strains JM105 (Yanisch-Perron, et al., (1985) Gene, 33, 103–119) and UT5600 (Earhart, et al., (1979) FEMS Microbiol. Lett., 6, 277–280) were used. Plasmid pAeT42 containing the A. eutrophus H16 phbC gene coding for the PHA synthase is described in U.S. Pat. No. 5,245,023 to Peoples and Sinskey. pTrc99A was obtained from Pharmacia. Bacteria were grown in 2× TY media (16 g/L tryptone, 10 g/L yeast extract, 5 g/L NaCl) at 30° C. Ampicillin was used in a final concentration of 100 µg/mL. Antibodies to the PHA synthase-glutathione transferase fusion protein were prepared as described by Gerngross, et al., (1993) J. Bacteriol., 175, 5289–5293. The polymerase chain reaction (PCR) was performed using an Ericomp™ thermal cycler and Amplitaq™ reagent kit from Perkin Elmer. Sequencing of protein was carried out by the MIT Biopolymer Laboratory. FPLC chromatography was carried out on a system purchased from Pharmacia.

Preparation of [3-$^3$H]HBCoA$^2$: [1-$^3$H]-D-Glucose (100 µcurie), 0.2 µmol NADP$^+$, 3 µmol acetoacetyl-CoA and 3.5 µmol D-glucose were dissolved in 1 mL of 20 mM Tris·HCl (pH 8.0) at 25° C. Glucose dehydrogenase (5 units) was added followed by 20 units of acetoacetylCoA reductase. The mixture was incubated for 2 h at room temperature. The pH of the solution was then adjusted to 4.5 with 1 M HCl and the reaction mixture was purified in 200 µL aliquots by loading onto 1 mL C18 Sep-Pak™ cartridges and washing with 1 mL of 50 mM KPi 9pH 4.7). The product was eluted with 1 mL of the same buffer containing 25% methanol. The fractions containing [3-$^3$H]-HBCoA were pooled, lyophilized, and stored as a 12 mM stock solution in 50% ethanol at −20° C. The concentration was determined by $A_{260nm}$ ($\epsilon$=16.4 mM$^{-1}$) (Ploux, et al., 1988) and by the coupled assay procedure described by Saito, et al., (1977) Arch. Microbiol., 114, 211–217.

I. Redesigning the PHA Synthase Gene for Overexpression

Routine DNA manipulations were carried out as described by Sambrook, et al., (1987) Molecular Cloning: a Laboratory Manual, Cold Spring Harbor, Cold Spring Harbor, N.Y. pTrc99A (1 µg) was digested with NcoI (10 units) for 1 h as described by the vendor. NcoI is a unique restriction site in the polylinker region of this plasmid. The resulting linearized DNA with recessed ends was made blunt ended using the Klenow fragment (2 units) after incubation with 0.2 mM dNTPs for 15 min. The DNA was then recirculalized using T4 DNA ligase (2 units) and the resulting plasmid pTrcN transformed into E. coli JM105. This process removes the ATG start codon immediately downstream of the ribosomal binding site in the vector. pTrcN was characterized by restriction digest analysis subsequent to its isolation and used in the development of the new expression vector described subsequently. The 5'-region of the phbC gene was modified using the PCR. Primer 1: CCGAATTCAGGAG-GTTTTTATTATGGCTACCGGCAAAGGCGCGG CAGCTTCCACGC (Sequence ID No. 1) and primer 2: CGTGCAGCGGA CCGGTGGCCTCGGC CTTGCCC (Sequence ID No. 2) were incubated with pAeT42 DNA linearized by digestion with SmaI. Primer 1 was designed to re-engineer the 5' end of the phbC gene and contains an EcoRI restriction site immediately upstream of an efficient E. coli ribosome binding region. Primer 2 is downstream of the NotI site (bps 265–297). The 316 bp amplified fragment was prepared using 35 cycles of the following program: denaturation at 95° C., 30 sec; annealing at 55° C., 60 sec; elongation at 72° C., 60 sec. Following amplification, the DNA was purified by phenol extraction and ethanol precipitation in the presence of 0.3 M NaOAc. The DNA (1 µg) was digested to completion with EcoRI (20 units) and NotI (20 units) for 2 h. Following electrophoresis in a 1.8% agarose gel, the DNA band was visualized by ethidium bromide staining and UV light, and the gel slice was excised.

The 161 bp EcoRI-NotI DNA fragment was recovered from the gel slice and purified using a Qiagen™ kit (Qiagen Inc., Calif.). The 161 bp piece (200 ng) was used in a three piece ligation with the 1560 bp fragment (200 ng) isolated from the restriction digest of pAeT42 with NotI and StuI and the 4.2 kb fragment (100 ng) of DNA resulting from restriction digestion of pTrcN with EcoRI and SmaI followed by alkaline phosphatase treatment. The fragments were ligated with 2 units of T4 DNA ligase for 16 h at 22°

C. This reaction mixture was used directly to transform competent *E. coli* JM105 cells and the resulting transformants selected on 2xTY agar plates containing 100 μg/mL of ampicillin.

The resulting plasmid, pKAS4, was isolated and characterized by both restriction digest maps and DNA sequencing using the dideoxy chain termination method and Sequenase™ II kits (United States Biochemical Corp.).

Optimization of the Expression of PHA Synthase Analyzed by Immunoblotting

*E. coli* JM105 harboring pKAS4 was grown at 30° C. At various times during the growth 100 μL aliquots were removed and the cells pelleted by centrifugation. The cells were suspended in 25 μL of SDS-PAGE buffer (Laemlli, 1970) and incubated for 5 min in a boiling $H_2O$ bath. The entire sample was then loaded onto a 4–15% gradient polyacrylamide gel (Biorad, Richmond, Calif.) and the proteins separated by SDS-PAGE. The proteins were transferred onto nitrocellulose filters (BA85, 0.45 μm pore size, Schleicher and Schuell) using a Mini Trans-Blot Cell (Biorad). Electroelution proceeded for 1 h at 300 mA in 25 mM Tris, 192 mM glycine, 20% (v/v) methanol. Following transfer, the filters were blocked with TBST (10 mM Tris, 150 mM NaCl, 0.05% Tween™ 20) containing 3% nonfat dry milk for 1 h. The anti-PHA synthase antibody (diluted 1 to 2000) in TBST was then incubated with the filters for 1 h and washed three times with TBS (TBST minus Tween™ 20). The protein cross reacting with the anti-PHA synthase antibodies was visualized using goat anti-rabbit IgG horse radish peroxidase (HRP) conjugate and the standard HRP color development reagent (Biorad).

Alternatively, proteins were electroblotted onto polyvinylidene difluoride (PVDF) membranes in 10 mM CHAPS (pH 11) and 10% $CH_3OH$ and were subjected to sequence analysis by the automated gas phase Edman degradation sequencing method (Matsudaira, (1987) J. Biol. Chem., 262, 10035–10038).

Results of Overproduction of the *A. eutrophus* PMA Synthase in *E. coli*

In an effort to increase the level of expression of the phbC gene product in *E. coli*, the *A. eutrophus* ribosome binding site was replaced with a strong consensus *E. coli* ribosome binding site and an eight base pair spacer, rich in Ts and As, upstream of the ATG initiation codon. Other appropriate consensus ribosome binding sites for other expression systems are known and could have been substituted for the *E. coli* ribosome binding sites. In addition, the third nucleotide of the second codon was changed from GCG (ala) to GCT (ala) (Bagdasarian, et al., (1983) Gene, 26, 273–282). PCR primers were used to generate a 161 bp fragment which was then used to modify the N terminus of the PHA synthase gene. The modified PHA synthase gene was then placed downstream of the IPTG-inducible trc promoter in the vector pTrcN to produce a new vector pKAS4, as shown in FIG. 1. Other inducible promoters are also known and could have been substituted for IPTG. This plasmid was transformed into *E. coli* JM105 and upon induction with IPTG, both analysis by Western blotting subsequent to SDS-PAGE and assay for catalytic activity revealed production of significant levels of soluble PHA synthase.

However, Western blotting analysis of the crude cell lysates revealed that subsequent to induction, in addition to the expected 64 kDa protein, there was the unexpected production of a second major protein of Mr=50 kDa and several other smaller proteins. When this experiment was repeated using cells directly boiled in SDS and not subjected to cell lysis, only the 64 kda protein was apparent. These results suggested that subsequent to cell lysis, proteolysis was occurring to degrade the PHA synthase. To test this hypothesis and to define the position of proteolysis, the 50 kDa protein was electroblotted onto a PVDF membrane (Matsudaira, 1987) and the first ten amino acids of its N-terminal sequence determined. As predicted by the antibody analysis, the 50 kDa protein results from a proteolytic clip of the 64 kDa protein between residues 100 and 101 ($L_{95}$-H-D-$R_{101}$-F-A-G). A search of the sequence specificity of the known *E. coli* proteases suggested that this cleavage could have been perpetrated by the ompT gene product, a protease found in the *E. coli* outer membrane (Sugimura & Nishihara, (1988) J. Bacter., 170, 5625–5632; Earhart, et al., 1979). Degradation of PHA synthase by this protease is consistent with the observation that proteolysis appears to occur only after cell lysis.

In order to test this hypothesis and more importantly to prevent proteolysis of the synthase, plasmid pKAS4 was transformed into the *E. coli* ompT-strain, UT5600. The cells were grown and induced with IPTG and analyzed for proteolysis by Western blotting. The results indicate that the proteolysis has been eliminated. Furthermore, these results have been substantiated by the increase in specific activity of the synthase in crude cell extracts relative to *E. coli* JM105 as described subsequently.

Example 2: Purification and characterization of PHA Synthase from *E. coli* UT5600

The electroblotting procedure accompanied by analysis with anti-PHA synthase antibodies or protein sequencing revealed that in *E. coli* JM105, extensive proteolysis accompanied the overexpression of the synthase. pKAS4 was therefore transformed into *E. coli* UT5600 and isolated from this strain. The cells were grown at 30° C. to an $A_{600}$ of 0.5 to 0.6 and subsequently induced by the addition of IPTG to a final concentration of 0.4 mM. The cells were then grown for an additional 4 h at 30° C. The doubling time is typically 50 min and yields of 8.2 g of cells per L of culture were obtained. The cells were harvested by centrifugation at 5000× g for 10 min at 4° C. and stored at −80° C. Cells can be stored under these conditions for months without detectable loss of activity. All purification steps were carried out at 4° C. unless otherwise stated. Cells (8.2 g) were suspended in 55 mL of 50 mM KPi (pH 7.0) containing 5% glycerol and lysed by either sonication or by use of the French Press. In the former case, lysis occurred using a Sonicator (Ultrasonic Processor xL; Farmingdale, N.Y.) turned on for 0.8 sec on a power setting of 9 to 10, then, turned off for 0.2 sec, and this process was repeated over a total period of 90 sec. The sample was continually cooled in an ice-salt bath and the temperature was monitored and not allowed to exceed 4° C.

Alternatively, the cells can be lysed by two passages through a French pressure cell at 16,000 psi and 4° C. The cell debris is then removed by centrifugation at 12,000 xg for 15 min. The supernatant is isolated, filtered through a 0.45 μm membrane, made 0.05% (w/v) in Hecameg™ and loaded directly onto a hydroxylapatite column (1.6×37 cm) which has been previously equilibrated for 30 min with 10 mM KPi (pH 7), 5% glycerol and 0.05% Hecameg™ (Buffer A) (flow rate 3 mL/min). The column is washed with 140 mL of Buffer A subsequent to loading and eluted with a 200×200 mL linear gradient from 10 to 300 mM KPi-Buffer A. Fractions, 10 mL, were collected and the synthase eluted between 110 and 150 mM KPi in 40 to 50 mL. The fractions containing activity can be pooled and rapidly frozen (liquid nitrogen) without significant loss in activity. This material (10 mL) in 130 mM KPi can be directly loaded onto a Q-Sepharose™ high performance FPLC column (t.25 mL) which has been previously equilibrated with 40 mL of 50 mM Tris·HCl (pH 8.5 at pH 4° C.), 5% glycerol and 0.05% Hecameg™ (Buffer B). Subsequent to loading, the column is washed with 25 mL of Buffer B at a flow rate of 1.2 mL/min and 5 mL fractions are collected. A 32.5×32.5 mL linear gradient from 0 to 1.5 M NaCl in Buffer B is then applied. Greater than 90% of PHA synthase elutes in fractions 2 and 3. Approximately 10% of the protein elutes in fractions 11 and 12 at 500 mM NaCl. The fractions are pooled and concentrated to 2.2 mg/mL using a YM 30 membrane and an Amicon filtration apparatus. The protein is Based on Coomassie staining of the protein in the crude cell extracts subsequent to SDS-PAGE, it was anticipated that a purification of approximately 20 fold would be required to obtain homogeneous protein. The protein isolated from the Q Sepharose™ column has a specific activity of 5 μmol $min^{-1}$ $mg^{-1}$ and upon freezing and thawing its activity increases to 8 μmol $min^{-1}$ $mg^{-1}$, a 16-fold overall purification. The enzyme is stable when rapidly frozen in liquid nitrogen for a period of at least a month.

TABLE 1

| Step | Purification of PHA Synthase[a] | | | | | | |
|---|---|---|---|---|---|---|---|
| | Volume mL | Total Units | Specific Activity | Protein mg | Protein mg/mL | Recovery % | Purification |
| crude | 50 | 166 | 0.51 | 325 | 6.5 | — | |
| HA[b] | 40 | 70 | 2.5 | 28 | 0.7 | 42 | 4.9 |
| A-Sep[c] | 40 | 40 | 5.0 | 8 | 0.14 | 24 | 9.8 |
| frozen & reassayed | 40 | 64 | 8.0 | 8 | 0.14 | 38.5 | 15.7 |

[a]from 8.2 g of wet bacteria.
[b]hydroxylapatite.
[c]normalized as only ¼ of the active HA fractions were loaded on the Q-Sepharose column at a time.

then rapidly frozen in liquid nitrogen and stored at −80° C. The protein is stable for at least a month under these conditions. An identical protocol was used to purify the mutant synthases described below.

Results of Purification of PHA Synthase

Numerous investigators over the past decades have attempted to purify PHA synthases, both the soluble and granule bound forms, from a variety of sources. The most successful attempt at purification of the soluble form from *A. eutrophus* was reported by Haywood, et al. (1989). Subsequent to two column chromatographic procedures, they reported a specific activity of 0.05 μmol $min^{-1}$ $mg^{-1}$ with a 2% recovery of total units. Tomita, et al. (1983) have partially purified the soluble form of synthase from *Z. ramigera*, also with a 2% recovery of total units and a specific activity of 1.1 μmol $min^{-1}$ $mg^{-1}$. In both cases the enzyme preparation was reported to be unstable, precluding its characterization or mechanistic studies.

The results of the purification of the *A. eutrophus* synthase expressed in *E. coli* are summarized in Table I. SDS-gradient gels (4 to 15%) were also used to characterize the purification of PHA synthase.

In the crude extracts the activity is 10-fold higher than the "purified" preparation of Haywood, et al. (1989) and within a factor of two of the "purified" soluble synthase from *Z. ramigera* (Tomita, et al., 1983). With the re-engineered gene, in the crude extract, the activity is remarkably stable, losing only 50% of the initial activity after standing at 4° C. for 24 hours. Initial efforts to purify this protein resulted in substantial losses in activity and very broad peaks of activity from almost all chromatographic materials investigated. After extensive experimentation with a variety of detergents, it was discovered that addition of Hecameg™ enhanced recovery of material from the columns and decreased the elution volumes. Therefore, all buffers were made 0.05% in Hecameg™.

FPLC, providing rapidity of purification, and a variety of anion exchange materials including hydroxylapatite and Q-Sepharose™, were used to purify the synthase to greater than 90% homogeneity with a 40% recovery of overall units.

Molecular Weight Determinations

Subunit molecular weight was determined using SDS-PAGE by the procedure of Laemmli (1970). The molecular weight standards included phosphorylase b (97.4 kDa), bovine serum albumin (68 kDa), ovalbumin (43 kDa), carbonic anhydrase (29 kDa), and β-lactalbumin (18.4 kDa). The native molecular weight was examined using FPLC chromatography on a Superdex 200 (Pharmacia) column. Synthase (2.2 mg/ml or 0.1 mg/mL) was loaded onto the column equilibrated in 150 mM NaCl, 25 mM Tris (pH 7.5) and 5% glycerol. The following molecular weight standards were used: ribonuclease A (13.7 kDa), chymotrypsinogen (25 kDa), bovine serum albumin (68 kDa), aldolase (158 kDa), catalase (232 kDa), ferritin (440 kDa), and thyroglobulin (669 kDa). The results are shown in FIG. 2.

The subunit molecular weight of the synthase based on SDS-PAGE is 64 kDa, similar to the Mr of 63.9 kDa defined by the gene sequence. Previous studies by Haywood, et al. (1989) to assess the native molecular weight of the synthase used crude enzyme isolated from *A. eutrophus*. Values of 150 to 170 kDa using gel filtration analysis and sucrose gradient ultracentrifugation, respectively, were reported. The molecular weight of the synthase isolated from its natural host, however, could be problematic as tightly bound proteins or tightly or covalently bound oligomeric or polymeric-β-hydroxybutyrate (PHB) could co-purify. Isolation of the enzyme from *E. coli* eliminates this complication.

Studies of the native molecular weight based on Superdex™ 200 size exclusion chromatography reveals molecular weights for the synthase of 60 KDa and 139 KDa. The fractions containing the putative monomer and dimer were concentrated and further analyzed by Western blotting. The proteins in both fractions cross react with antibodies raised to the PHA synthase and indicated a protein of 64 kDa. In addition, each fraction contained polymerase activity. Concentration of each fraction followed by rechromatography revealed the same monomer, dimer mixture. Thus, the protein as isolated from *E. coli* exists as an equilibrium between monomeric and dimeric forms.

PHA Synthase Assays (a) Extraction with $CHCl_3$

This method is a modification of the one described by Fukui, et al. (1976) Arch. Microbiol., 110, 149–156. A typical assay mixture contained in a final volume of 40 µL: 143 mM KPi (pH 7.0), 0.62 mM [$3^{-3}$H]-3-D-HBCoA (specific activity $1.1 \times 10^6$ cpm/µmol) and variable amounts of PHA synthase (0.07 to 10 µg), depending on the purity. The reactions were started by addition of enzyme after equilibration of the substrate in the buffer for 10 min at 25° C. The reaction mixtures were then incubated at 25° C. for 1 to 30 min. The reactions are stopped by addition of 100 µL of ice-cold 5% trichloroacetic acid with vortexing. The solution is then extracted with 0.5 mL of $CHCl_3$. The layers are allowed to separate, the protein is at the interface, and 0.4 mL of the $CHCl_3$ layer is transferred to a scintillation vial and the $CHCl_3$ evaporated under a stream of argon. The PHA extracted is then quantified by scintillation counting after addition of 8 mL of Scint A-XF scintillation fluid.

(b) Loss of HBCoA monitored spectrophotometrically

HBCoA has been reported by Fukui, et al., (1976) to have an absorption max at 232 nm and an $\epsilon = 4.5 \times 10^3$ $M^{-1}$ $cm^{-1}$. With purified synthase the decrease in absorbance at 232 nm can be monitored spectrophotometrically and continually.

(c) Formation of -SCOA monitored using Ellman's Reagent

Coenzyme A released during the PHA synthase catalyzed reaction can be measured using Ellman's reagent, 5,5'-dithiobis(2-nitrobenzoic acid) (DTNB) (Ellman, (1959) Arch. Biochem. Biophys., 82, 70–77). A typical reaction mixture (360 µL) contained 1.0 mM HBCoA and 143 mM KPi (pH 7.0). The assay mixture was preincubated for ten min at 25° C. after which time the reaction was started by the addition of enzyme. Aliquots (40 µL) were removed at timed intervals and stopped by addition of 100 µL of 5% trichloroacetic acid. The precipitated protein was pelleted by centrifugation for 10 min and an aliquot (125 µL) of supernatant was added to 675 µL of 500 mM KPi (pH 7.5)/ DTNB [10 µL of a 10 mM stock solution in 500 mM KPi (pH 7.5)] was added to this mixture and incubated for two min at room temperature. The absorbance at 410 nm ($\epsilon = 13.7$ $mM^{-1}$) was measured.

Previous workers have used a discontinuous assay to monitor PHA production incubation of [$^3$H]-HBCoA with synthase for various time periods (Fukui, et al., 1976). The reactions are stopped by addition of trichloroacetic acid and then the product is extracted into $CHCl_3$. The $CHCl_3$ is then removed and the residue quantitated by scintillation counting. Results of a typical assay are shown in FIG. 3a. At each concentration of protein examined, there is a lag phase which precedes the linear phase of product formation. The lower the concentration of the protein, the longer the lag phase.

Figure 3B:
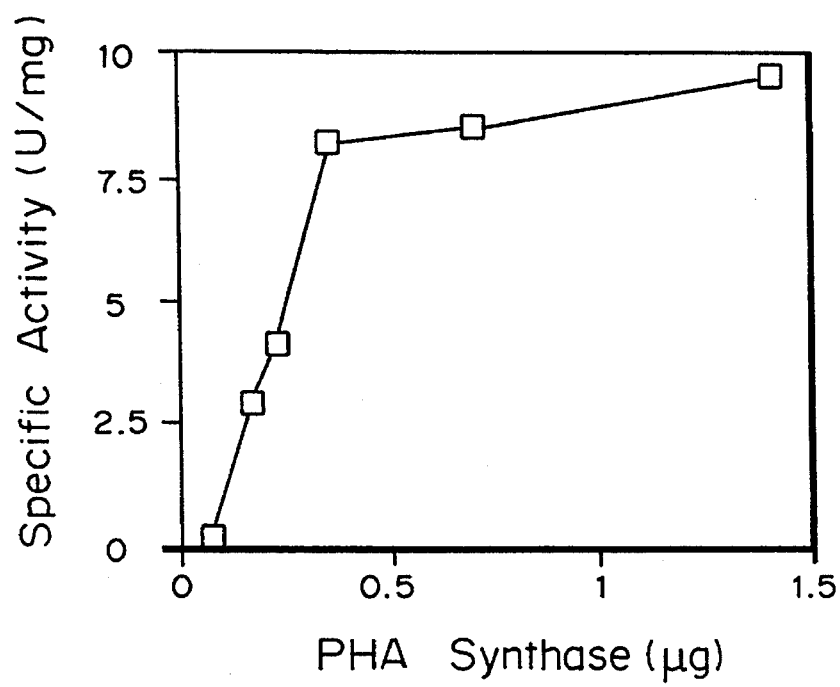
FIG. 3b is a graph of the determination of the specific activity of PHA synthase as a function of protein concentration.
Figure 4:
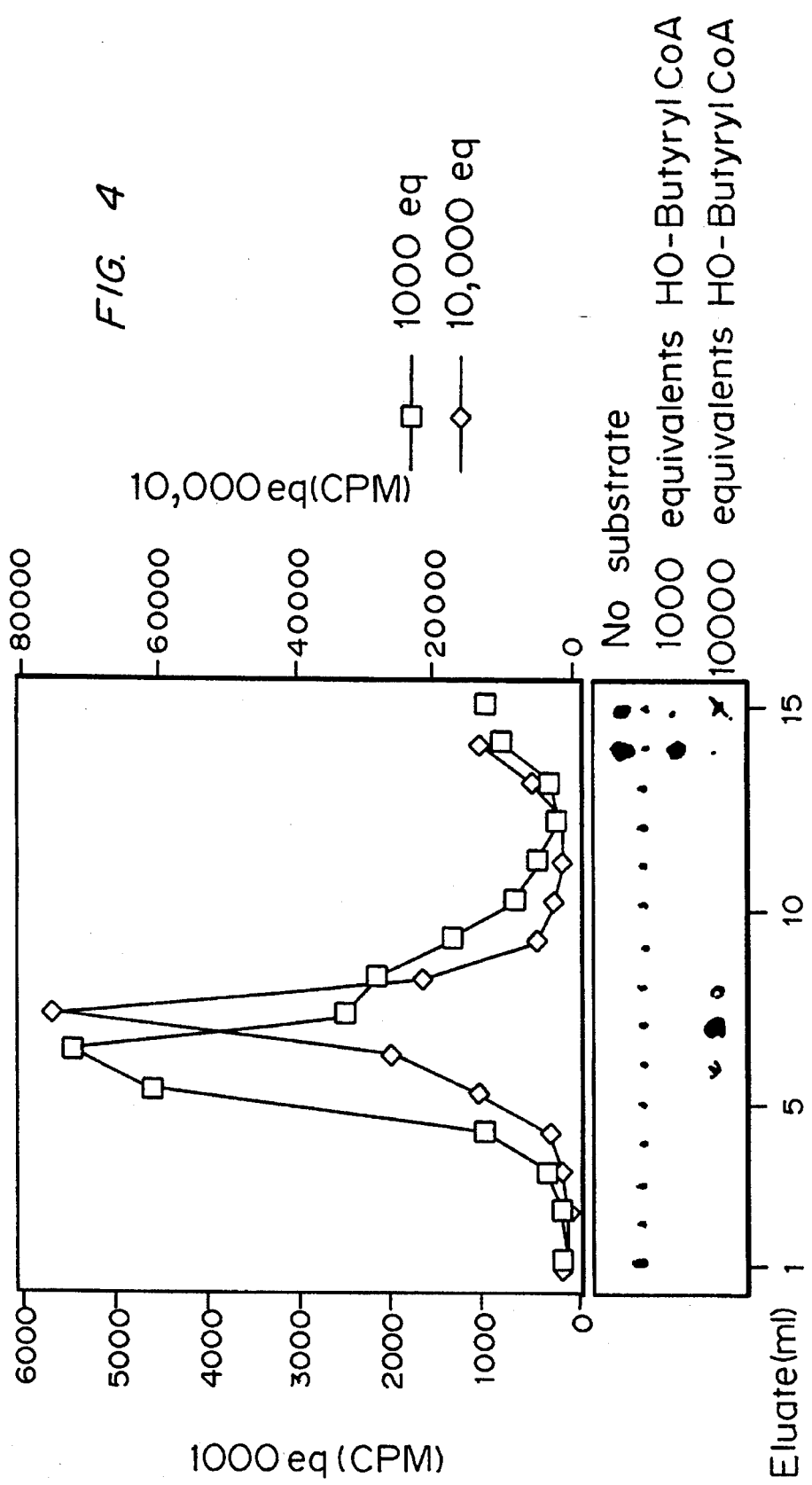
FIG. 4 is a graph of the sucrose-density centrifugation of PHA synthase incubated with 0, 1000, and 10,000-fold excess of [$^3$H]-HBCoA relative to protein. For the 1000-fold excess substrate, the scale is on the left (open squares). For the 10,000-fold excess, the scale is on the right (open diamonds). The bottom panel uses dot blots and PHA synthase antibody to determine the location of the synthase.

The rates of the reaction used to calculate the specific activities reported in Table I have been determined by analyzing the linear part of the curve subsequent to the lag phase. The dependence of the specific activity of the protein on the protein concentration is shown in FIG. 3b. These results establish that during the purification of the synthase care must be taken to appropriately adjust the concentrations of synthase in the assay mixture and a full-time course for PHA production is required to insure that one avoids measuring the turnover in the lag phase of the reaction. The assays using purified synthase monitoring $CHCl_3$ extractable polymer agree within 10% with the assays monitoring hydrolysis of 3-D-HBCoA as a change in the absorbance at 232 nm or formation of thiolate of coenzyme A using Ellman's reagent (1959).

Characterization of the PHA Product by Size Exclusion Chromatography

Assay mixtures, 50 µL, containing PHA synthase and [$^3$H]-HBCoA, subsequent to reaction for 30 min, were incubated with pronase (0.1 unit) in 140 mM KPi (pH 7.0) for 10 min at 25° C. The reaction was stopped by the addition of 0.5 mL $CHCl_3$ and the polymer was extracted by vortexing for 1 min. The $CHCl_3$ phase was dried over $MgSO_4$, filtered through glass wool, and evaporated to less than 100 µL. This solution was injected directly onto a PlGel Mixed C column, and chromatographed using $CHCl_3$ as eluate at a flow rate of 1 mL/min. For calibration, polystyrene standards of low polydispersity (Mr 600 Da to 1,860 kDa) were used (Polysciences, Inc., Warrington, Pa.). Fractions eluted from the column were analyzed by scintillation counting.

Abbreviations used in the foregoing description are: PHA, polyhydroxyalkanoate; PHB, polyhydroxybutyrate; wt, wild-type; IPTG, isopropylthio-β-D-galactosidase; Hecameg™, 6-O-(N-heptylcarbamoyl)-methyl-α-D-glucopyranoside; 3-D-HBCoA, hydroxybutyrylCoA; PCR, polymerase chain reaction; SDS-PAGE, sodium dodecylsulfatepolyacrylamide gel electrophoresis; TBST, 10 mM Tris, 150 mM NaCl, 0.05% Tween™ 20; HRP, horse radish peroxidase; PVDF, polyvinylidene difluoride; DTNB, 5,5'-dithiobis(2-nitrobenzoic acid); KPi, potassium phosphate.

Modifications and variations of the present invention will be obvious to those skilled in the art from the foregoing detailed description and are intended to come within the scope of the following claims.

We claim:

1. A method for the overproduction and purification of soluble polyhydroxyalkanoate (PHA) synthase expressed from an isolated structural gene comprising expressing the isolated structural gene encoding the synthase in a vector in an expression system not expressing an enzyme cleaving the synthase selected from the group consisting of bacteria, yeast, fungi, and plants.

2. The method of claim 1 further comprising placing the PHA synthase gene under the transcriptional control of a regulatable promoter.

3. The method of claim 2 wherein the promoter is selected from the group consisting of an IPTG inducible promoter, lacZ, tac, trc, the trp promoter, the temperature inducible phage promoter lambda $P_L$, and a phage T7 promoter/T7 RNA polymerase system.

4. The method of claim 1 where the PHA synthase is a polyhydroxyalkamoate (SCPHA) synthase.

5. The method of claim 1 where the PHA synthase is a SCPHA synthase from *Alcaligenes eutrophus*.

6. The method of claim 1 where the PHA synthase is a polyhydroxyalkanoate (LCPHA) synthase.

7. The method of claim 1 where the PHA synthase is a LCPHA synthase encoded by a gene from Pseudomonas.

8. The method of claim 1 where the PHA synthase is overproduced in a host selected from the group including bacteria, yeast, fungi and plants and the vector comprises a ribosome binding site enhancing expression in the host.

9. The method of claim 1 where the PHA synthase is overproduced in a bacterial host.

10. The method of claim 1 where the PHA synthase is overproduced in *Escherichia coli*.

11. The method of claim 10 where the PHA synthase is overproduced in a protease deficient strain of *Escherichia coli*.

12. The method of claim 11 where the PHA synthase is expressed in an ompT deficient *Escherichia coli* strain.

13. The method of claim 10 where the PHA synthase is engineered so as to remove cleavage sites that are normally cleaved by proteases in the naturally occurring synthase.

14. The method of claim 1 further comprising purifying the PHA synthase by chromatography using buffer solutions containing detergents.

15. The method of claim 14 where the PHA synthase is purified by chromatography using buffer solutions containing 6-O-(N-heptylcarbamoyl)-methyl-$\alpha$ -D-glucopyranoside.

16. The method of claim 15 wherein the synthase is purified by chromatography on hydroxyapatite.

17. An expression system for the overproduction and purification of soluble PHA synthase expressed from an isolated structural gene comprising a host not expressing an enzyme cleaving the synthase selected from the group consisting of bacteria, yeast, fungi, and plants, and the isolated structural gene encoding PHA synthase in a vector for expression of the synthase in the host.

18. The system of claim 17 wherein the PHA synthase gene is under the transcriptional control of a regulatable promoter.

19. The system of claim 17 where the PHA synthase is selected from the group consisting of SCPHA synthase and LCPHA synthase.

20. The system of claim 17 where the PHA synthase is overproduced in a bacterial host.

21. The system of claim 17 where the PHA synthase is overproduced in *Escherichia coli*.

22. The system of claim 17 where the PHA synthase is overproduced in a protease deficient strain of *Escherichia coli*.

23. The method of claim 17 where the PHA synthase is engineered so as to remove cleavage sites that are normally cleaved by proteases in the naturally occurring synthase.

* * * * *

UNITED STATES PATENT AND TRADEMARK OFFICE
CERTIFICATE OF CORRECTION

PATENT NO.   : 5,480,794
DATED         : January 2, 1996
INVENTOR(S)  : Oliver P. Peoples; Tillman U. Gerngross; Anthony J. Sinskey It is certified that error appears in the above-identified patent and that said Letters Patent is hereby corrected as shown below:

Column 2,
Line 11, cancel "for" and insert -- or --.
Lines 13-15, that portion of the formula reading "CH2COSCoA" should read -- CH3COSCoA --.
Lines 13-15, that portion of the formuls reading "NADP" should read -- NADP+ --.
Lines 13-15, the two portions of the formula reading "===" should read --    --

Claim 4, column 15,
Line 45, cancel "polyhydroxyalkamoate" and insert -- short chain polyhydroxyalkanoate --.

Claim 6, column 15,
Line 49, insert between "a" and "polyhydroxyalkanoate" -- long chain --.

Column 14,
Lines 41-42, cancel "dodecvlsulfatepolyacrylamide" and insert -- dodecylsulfate-polyacrylamide --.

Signed and Sealed this

Second Day of October, 2001

Attest:

NICHOLAS P. GODICI
Attesting Officer    Acting Director of the United States Patent and Trademark Office